US008712697B2

(12) United States Patent
Struble et al.

(10) Patent No.: US 8,712,697 B2
(45) Date of Patent: *Apr. 29, 2014

(54) DETERMINATION OF COPY NUMBER VARIATIONS USING BINOMIAL PROBABILITY CALCULATIONS

(75) Inventors: Craig Struble, San Jose, CA (US); John Stuelpnagel, San Jose, CA (US)

(73) Assignee: Ariosa Diagnostics, Inc., San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/605,505

(22) Filed: Sep. 6, 2012

(65) Prior Publication Data

US 2013/0060483 A1    Mar. 7, 2013

Related U.S. Application Data

(60) Provisional application No. 61/531,738, filed on Sep. 7, 2011.

(51) Int. Cl.
*G01N 33/50* (2006.01)
*G06F 19/18* (2011.01)

(52) U.S. Cl.
CPC ..................................... *G06F 19/18* (2013.01)
USPC .......................................................... 702/19

(58) Field of Classification Search
None
See application file for complete search history.

(56) References Cited

U.S. PATENT DOCUMENTS

| | | | |
|---|---|---|---|
| 4,683,195 A | 7/1987 | Mullis et al. |
| 4,988,617 A | 1/1991 | Landegren et al. |
| 5,143,854 A | 9/1992 | Pirrung et al. |
| 5,242,794 A | 9/1993 | Whiteley et al. |
| 5,270,184 A | 12/1993 | Walker et al. |
| 5,399,491 A | 3/1995 | Kacian et al. |
| 5,409,818 A | 4/1995 | Davey et al. |
| 5,413,909 A | 5/1995 | Bassam et al. |
| 5,422,252 A | 6/1995 | Walker et al. |
| 5,437,975 A | 8/1995 | McClelland |
| 5,494,810 A | 2/1996 | Barany et al. |
| 5,547,839 A | 8/1996 | Dower et al. |
| 5,554,517 A | 9/1996 | Davey et al. |
| 5,578,832 A | 11/1996 | Trulson et al. |
| 5,631,734 A | 5/1997 | Stern et al. |
| 5,648,245 A | 7/1997 | Fire et al. |
| 5,800,992 A | 9/1998 | Fodor et al. |
| 5,808,041 A | 9/1998 | Padhye et al. |
| 5,830,711 A | 11/1998 | Barany et al. |
| 5,834,758 A | 11/1998 | Trulson et al. |
| 5,856,092 A | 1/1999 | Dale et al. |
| 5,861,245 A | 1/1999 | McClelland et al. |
| 5,871,928 A | 2/1999 | Fodor et al. |
| 5,874,219 A | 2/1999 | Rava et al. |
| 5,888,740 A | 3/1999 | Han |
| 5,898,071 A | 4/1999 | Hawkins |
| 5,902,723 A | 5/1999 | Dower et al. |
| 5,936,324 A | 8/1999 | Montagu |
| 5,952,170 A | 9/1999 | Stroun et al. |
| 5,981,956 A | 11/1999 | Stern |
| 6,025,601 A | 2/2000 | Trulson et al. |
| 6,027,889 A | 2/2000 | Barany et al. |
| 6,045,996 A | 4/2000 | Cronin et al. |
| 6,054,564 A | 4/2000 | Barany et al. |
| 6,063,603 A | 5/2000 | Davey et al. |
| 6,090,555 A | 7/2000 | Fiekowsky et al. |
| 6,141,096 A | 10/2000 | Stern et al. |
| 6,156,504 A | 12/2000 | Gocke et al. |
| 6,185,030 B1 | 2/2001 | Overbeck |
| 6,201,639 B1 | 3/2001 | Overbeck |
| 6,210,891 B1 | 4/2001 | Nyren et al. |
| 6,218,803 B1 | 4/2001 | Montagu et al. |
| 6,225,625 B1 | 5/2001 | Pirrung et al. |
| 6,258,540 B1 | 7/2001 | Lo et al. |
| 6,268,148 B1 | 7/2001 | Barany et al. |
| 6,309,824 B1 | 10/2001 | Drmanac |
| 6,310,199 B1 | 10/2001 | Smith et al. |
| 6,312,892 B1 | 11/2001 | Barany et al. |
| 6,316,229 B1 | 11/2001 | Lizardi et al. |
| 6,329,179 B1 | 12/2001 | Kopreski |
| 6,342,387 B1 | 1/2002 | Hayashizaki et al. |
| 6,386,749 B1 | 5/2002 | Watts et al. |
| 6,391,623 B1 | 5/2002 | Besemer et al. |
| 6,401,267 B1 | 6/2002 | Drmanac |
| 6,410,276 B1 | 6/2002 | Burg et al. |
| 6,506,594 B1 | 1/2003 | Barany et al. |
| 6,534,262 B1 | 3/2003 | McKernan et al. |
| 6,534,293 B1 | 3/2003 | Barany et al. |
| 6,562,573 B2 | 5/2003 | Halaka |

(Continued)

FOREIGN PATENT DOCUMENTS

| | | |
|---|---|---|
| GB | 970444 | 9/1964 |
| GB | 2299166 | 9/1996 |

(Continued)

OTHER PUBLICATIONS

Tomilin, et al., "Mechanisms of Chromosome Destabilization in Human Cells", Sov. Sci. Rev. D. Physiochem. Biol., 10:39-89 (1992).
Ulbright, "Germ cell tumors of the gonads: a selective review emphasizing problems in differential diagnosis, newly appreciated, and controversial issues," Modern Pathology, 18:S61-S79 (2005).
Vasioukhin, et al., "Point mutations in the N-ras gene in the blood plasma DNA of patients with myelodysplastic syndrome or acute myelogenous leukaemia", British J. of Haematology, 86:774-79 (1994).
Walker, et al., "Human DNA quantitation using Alu element-based polymerase chain reaction", Analytical Biochem., 315:122-28 (2003).
Witt, et al., "An improved, non-isotopic method of screening cells from patients with abnormalities of sexual differentiation for Y chromosomal DNA content", J. Med. Genet., 30:304-07 (1993).

(Continued)

*Primary Examiner* — Jason Sims
(74) *Attorney, Agent, or Firm* — Convergent Law Group LLP

(57) ABSTRACT

This invention relates to a binomial calculation of copy number of data obtained from a mixed sample having a first source and a second source.

7 Claims, 1 Drawing Sheet

(56) References Cited

U.S. PATENT DOCUMENTS

| | | | |
|---|---|---|---|
| 6,573,103 B1 | 6/2003 | Wald |
| 6,576,453 B2 | 6/2003 | Barany et al. |
| 6,797,470 B2 | 9/2004 | Barany et al. |
| 6,828,100 B1 | 12/2004 | Ronaghi |
| 6,833,246 B2 | 12/2004 | Balasubramanian |
| 6,852,487 B1 | 2/2005 | Barany et al. |
| 6,858,412 B2 | 2/2005 | Willis et al. |
| 6,864,052 B1 | 3/2005 | Drmanac et al. |
| 6,911,345 B2 | 6/2005 | Quake et al. |
| 6,914,137 B2 | 7/2005 | Baker |
| 6,927,028 B2 | 8/2005 | Dennis et al. |
| 6,949,370 B1 | 9/2005 | Barany et al. |
| 6,977,162 B2 | 12/2005 | Dhallan |
| 7,014,994 B1 | 3/2006 | Barany et al. |
| 7,083,917 B2 | 8/2006 | Barany et al. |
| 7,097,980 B2 | 8/2006 | Barany et al. |
| 7,166,434 B2 | 1/2007 | Barany et al. |
| 7,198,894 B2 | 4/2007 | Barany et al. |
| 7,208,274 B2 | 4/2007 | Dhallan |
| 7,232,656 B2 | 6/2007 | Balasubramanian |
| 7,244,233 B2 | 7/2007 | Krantz et al. |
| 7,244,831 B2 | 7/2007 | Barany et al. |
| 7,312,039 B2 | 12/2007 | Barany et al. |
| 7,315,787 B2 | 1/2008 | Orlandi et al. |
| 7,320,865 B2 | 1/2008 | Barany et al. |
| 7,332,277 B2 | 2/2008 | Dhallan |
| 7,332,285 B2 | 2/2008 | Barany et al. |
| 7,343,190 B2 | 3/2008 | Krantz et al. |
| 7,358,048 B2 | 4/2008 | Barany et al. |
| 7,364,858 B2 | 4/2008 | Barany et al. |
| 7,429,453 B2 | 9/2008 | Barany et al. |
| 7,442,506 B2 | 10/2008 | Dhallan |
| 7,455,965 B2 | 11/2008 | Barany et al. |
| 7,459,311 B2 | 12/2008 | Nyren et al. |
| 7,527,929 B2 | 5/2009 | McKernan et al. |
| 7,556,924 B2 | 7/2009 | Barany et al. |
| 7,582,420 B2 | 9/2009 | Oliphant et al. |
| 7,598,060 B2 | 10/2009 | Dhallan |
| 7,601,491 B2 | 10/2009 | Collis et al. |
| 7,622,281 B2 | 11/2009 | Ronaghi et al. |
| 7,645,576 B2 | 1/2010 | Lo et al. |
| 7,648,824 B2 | 1/2010 | Nyren et al. |
| 7,700,323 B2 | 4/2010 | Willis et al. |
| 7,709,194 B2 | 5/2010 | Lo et al. |
| 7,709,201 B2 | 5/2010 | Barany et al. |
| 7,718,367 B2 | 5/2010 | Lo et al. |
| 7,718,370 B2 | 5/2010 | Dhallan |
| 7,727,720 B2 | 6/2010 | Dhallan |
| 7,727,727 B2 | 6/2010 | Collis |
| 7,754,428 B2 | 7/2010 | Lo et al. |
| 7,780,600 B2 | 8/2010 | Krantz et al. |
| 7,799,531 B2 | 9/2010 | Mitchell et al. |
| 7,807,431 B2 | 10/2010 | Barany et al. |
| 7,888,017 B2 | 2/2011 | Quake et al. |
| 7,901,884 B2 | 3/2011 | Lo et al. |
| 7,989,614 B2 | 8/2011 | Deggerdal et al. |
| 8,008,018 B2 | 8/2011 | Quake et al. |
| 8,195,415 B2 | 6/2012 | Fan et al. |
| 8,296,076 B2 | 10/2012 | Fan et al. |
| 2002/0045176 A1 | 4/2002 | Lo et al. |
| 2002/0132241 A1 | 9/2002 | Fan et al. |
| 2003/0003459 A1 | 1/2003 | Stahl |
| 2003/0044388 A1 | 3/2003 | Dennis et al. |
| 2003/0054386 A1 | 3/2003 | Antonarakis et al. |
| 2003/0064366 A1 | 4/2003 | Hardin et al. |
| 2003/0108913 A1 | 6/2003 | Schouten |
| 2003/0143599 A1 | 7/2003 | Makarov et al. |
| 2004/0009518 A1 | 1/2004 | Lo et al. |
| 2004/0101835 A1 | 5/2004 | Willis et al. |
| 2004/0203037 A1 | 10/2004 | Lo et al. |
| 2004/0214175 A9 | 10/2004 | McKernan et al. |
| 2005/0095618 A1 | 5/2005 | Tsui et al. |
| 2005/0191656 A1 | 9/2005 | Drmanac et al. |
| 2006/0252068 A1 | 11/2006 | Lo et al. |
| 2006/0252071 A1 | 11/2006 | Lo et al. |
| 2006/0275789 A1 | 12/2006 | Willis et al. |
| 2007/0087345 A1 | 4/2007 | Olson-Munoz et al. |
| 2007/0207482 A1 | 9/2007 | Church et al. |
| 2007/0275402 A1 | 11/2007 | Lo et al. |
| 2008/0020390 A1 | 1/2008 | Mitchell et al. |
| 2008/0081338 A1 | 4/2008 | Lo et al. |
| 2008/0096766 A1 | 4/2008 | Lee |
| 2008/0206748 A1 | 8/2008 | Olson et al. |
| 2009/0018024 A1 | 1/2009 | Church et al. |
| 2009/0029377 A1 | 1/2009 | Lo et al. |
| 2009/0048124 A1 | 2/2009 | Leamon et al. |
| 2009/0061425 A1 | 3/2009 | Lo et al. |
| 2009/0087847 A1 | 4/2009 | Lo et al. |
| 2009/0155776 A1 | 6/2009 | Lo et al. |
| 2010/0105049 A1 | 4/2010 | Ehrich et al. |
| 2010/0105052 A1 | 4/2010 | Drmanac et al. |
| 2010/0112575 A1 | 5/2010 | Fan et al. |
| 2010/0112590 A1 | 5/2010 | Lo et al. |
| 2010/0120076 A1 | 5/2010 | Braun et al. |
| 2010/0136529 A1 | 6/2010 | Shoemaker et al. |
| 2010/0184043 A1 | 7/2010 | Mitchell et al. |
| 2010/0184044 A1 | 7/2010 | Mitchell et al. |
| 2010/0184210 A1 | 7/2010 | Rossmanith et al. |
| 2010/0267034 A1 | 10/2010 | Lo et al. |
| 2010/0291571 A1 | 11/2010 | Stoughton et al. |
| 2010/0291572 A1 | 11/2010 | Stoughton et al. |
| 2011/0003293 A1 | 1/2011 | Stoughton et al. |
| 2011/0027771 A1 | 2/2011 | Deng |
| 2011/0039724 A1 | 2/2011 | Lo et al. |
| 2011/0059451 A1 | 3/2011 | Mitchell et al. |
| 2011/0086357 A1 | 4/2011 | Lo et al. |
| 2011/0105353 A1 | 5/2011 | Lo et al. |
| 2011/0117548 A1 | 5/2011 | Mitchell et al. |
| 2011/0124518 A1 | 5/2011 | Cantor |
| 2011/0143342 A1 | 6/2011 | Lo et al. |
| 2011/0151442 A1 | 6/2011 | Fan et al. |
| 2011/0171638 A1 | 7/2011 | Stoughton et al. |
| 2011/0172111 A1 | 7/2011 | Cantor |
| 2011/0177517 A1 | 7/2011 | Rava et al. |
| 2011/0178719 A1 | 7/2011 | Rabinowitz |
| 2011/0183330 A1 | 7/2011 | Lo et al. |
| 2011/0201507 A1 | 8/2011 | Rava et al. |
| 2011/0224087 A1 | 9/2011 | Quake et al. |
| 2011/0230358 A1 | 9/2011 | Rava et al. |
| 2011/0245085 A1 | 10/2011 | Rava et al. |
| 2011/0276277 A1 | 11/2011 | Lo et al. |
| 2011/0288780 A1 | 11/2011 | Rabinowitz |
| 2011/0312503 A1 | 12/2011 | Chuu |
| 2012/0003650 A1 | 1/2012 | Lo et al. |
| 2012/0010085 A1 | 1/2012 | Rava |
| 2012/0100548 A1 | 4/2012 | Rava et al. |
| 2012/0108460 A1 | 5/2012 | Quake et al. |
| 2012/0165203 A1 | 6/2012 | Quake et al. |
| 2012/0190018 A1* | 7/2012 | Struble et al. ............ 435/6.11 |
| 2012/0225798 A1 | 9/2012 | Cantor et al. |
| 2012/0237928 A1 | 9/2012 | Rava et al. |
| 2012/0264115 A1 | 10/2012 | Rava |
| 2012/0264121 A1 | 10/2012 | Rava et al. |
| 2012/0270739 A1 | 10/2012 | Rava et al. |

FOREIGN PATENT DOCUMENTS

| | | |
|---|---|---|
| WO | WO87/06270 | 10/1987 |
| WO | WO90/06995 | 6/1990 |
| WO | WO99/47964 | 9/1999 |
| WO | WO03/038120 | 5/2003 |
| WO | WO2007/100243 | 9/2007 |
| WO | WO2007/126377 | 11/2007 |
| WO | WO2008/118998 | 10/2008 |
| WO | WO2009/036525 | 3/2009 |
| WO | WO2009/102632 | 8/2009 |
| WO | WO2011/090556 | 7/2011 |
| WO | WO2011/090557 | 7/2011 |
| WO | WO2011/090558 | 7/2011 |

OTHER PUBLICATIONS

International Search Report for PCT/US2011/046981, dated Oct. 15, 2012.

Final Office Action dated Dec. 7, 2012 on U.S. Appl. No. 13/013,732.

(56) References Cited

OTHER PUBLICATIONS

Final Office Action dated Oct. 12, 2012 on U.S. Appl. No. 13/013,732.
Heilig, et al., "The DNA sequence and analysis of human chromosome 14", Nature, 421:601-09 (2003).
Hosny, et al., "TP53 mutations in circulating fee DNA from Egyptian patients with non-Hodgkin's lymphoma", Cancer Lett., 275(2):234-39 (2009).
Irizarry, et al., "Summaries of Affymetrix GeneChip probe level data", Nuc. Acid Res., 31(4):e5 (2003).
Kamnasaran and Cox, "Current status of chromosome 14", J. Med. Genet., 39:81-90 (2002).
Landegren, et al., "A ligase-mediated gene detection technique", Science, 241:1077 (1988).
Leon, "Free DNA in the Serum of Cancer Patients and the Effect of Therapy", Cancer Res., 37:646-50 (1977).
Li, et al., "A photocleavable fluorescent nucleotide for DNA sequencing and analysis", PNAS USA, 100(2):414-19 (2003).
Liao, et al. "Targeted massively parallel sequencing of maternal plasma DNA permits efficient and unbiased detection of fetal alleles", Clin Che, 57:92-101 (2011).
Lo, et al., "Detection of single-copy fetal DNA sequence from maternal blood", The Lancet, 335:1463-64 (1990).
Lo, et al., "Two-way cell traffic between mother and fetus: biological and clinical implications", Blood, 88:4390-95 (1996).
Lo, et al., "Presence of fetal DNA in maternal plasma and serum", The Lancet, 350:485-86 (1997).
Lo, et al., "Quantitative analysis of fetal DNA in maternal plasma and serum: implications for noninvasive prenatal diagnosis", Am J. Hum. Genetics, 62:768-75 (1998).
Lo, et al., "Prenatal diagnosis of fetal RhD status by molecular analysis of maternal plasma", N. Engl J Med, 339:1734-38 (1998).
Lo, et al., "Rapid clearance of fetal DNA from maternal plasma", Am J. Hum. Genetics, 64:218-24 (1999).
Lo, et al., "Digital PCR for the molecular detection of fetal chromosomal aneuploidy", PNAS USA, 104:13116-21 (2007).
Lo, et al., "Plasma placental RNA allelic ratio permits noninvasive prenatal chromosomal aneuploidy detection", Nat. Med., 13:218-23 (2007).
Lo, et al., Maternal plasma DNA sequencing reveals the genome-wide genetic and mutational profile of the fetus. Sci Transl Med, 2:61ra91 (2010).
Lo, "Fetal nucleic acids in maternal blood: the promises", Clin. Chem. Lab Med., 50(5):xxx-xxx (DOI 10.1515/CCLM.2011.765) (2011).
Lun, et al., "Microfluidics Digital PCR Reveals a Higher than Expected Fraction of Fetal DNA in Maternal Plasma", Clin. Chem., 54(10):1664-72 (2008).
Lun, et al., "Noninvasive prenatal diagnosis of monogenic diseases by digital size selection and relative mutation dosage on DNA in maternal plasma", PNAS USA, 105(50):19920-25 (2008).
Makrigiorgos, et al., "A PCR-based amplification method retaining the quantitative difference between two complex genomes", Nat. Biotech., 20:936-39 (2002).
Mangs, Curr. Genomics, "The Human Pseudoautosomal Region (PAR): Origin, Function and Future", 8(2):129-36 (2007).
Mansfield, "Diagnosis of Down syndrome and other aneuploidies using quantitative polymerase chain reaction and small tandem repeat polymorphisms", Human Molecular Genetics, 2(1):43-50 (1993).
Mantzaris, et al., "Preliminary report: correct diagnosis of sex in fetal cells isolated from cervical mucus during early pregnancy", ANZJOG, 45(6):529-32 (2005).
Mujezinovic and Alfirevic, Obstet. Gynecol., "Procedure-Related Complications of Amniocentesis and Chorionic Villous Sampling: A Systematic Review", 110(3):687-94 (2007).
Mueller, et al., "Isolation of fetal trophoblast cells from peripheral blood of pregnant women", The Lancet, 336:197-200 (1990).
Nawroz, et al., "Microsatellite alterations in serum DNA of head and neck cancer patients", Nature Medicine, 2(9):1035-37 (1996).
Ng, et al., "mRNA of placental origin is readily detectable in maternal plasma", PNAS USA, 100:4748-53 (2003).
Page, et al., "Breakpoint diversity illustrates distinct mechanisms for Robertsonian translocation formation", Hum. Molec. Genet., 5(9):1279-88 (1996).
Page, et al., Br. J. Cancer, "Detection of HER2 amplification in circulating free DNA in patients with breast cancer", 104(8):1342-48 (2011).
Papageorgiou, et al., "DNA methylation ratio permits noninvasive prenatal diagnosis of trisomy 21", Nat. Med., 17:510-13 (2011).
Petersen, et al., "Down Syndrome Due to De Novo Robertsonian Translocation t(14q21q): DNA Polymorphism Analysis Suggests that the Origin of the Extra q21 is Maternal", Am. JU. Hum. Genet. 49:529-36 (1991).
Poon, et al., "Differential DNA methylation between fetus and mother as a strategy for detecting fetal DNA in maternal plasma", Clin Chem, 48:35-41 (2002).
Rijinders, et al., "Fetal sex determination from maternal plasma in pregnancies at risk for congenital adrenal hyperplasia", Obstet Gynecol, 98:374-78 (2001).
Ro, et al., "Association of Polymorphisms of Interleukin-8, CXCR1, CXCR2, and Selectin With Allograft Outcomes in Kidney Transplantation", Transplantation, 91(1):57-64 (2011).
Ross, et al., "The DNA sequence of the human X Chromosome", Nature 434:325-37 (2005).
Roth, et al., Molec. Oncol., "Screening for circulating nucleic acids and caspase activity in the peripheral blood as potential diagnostic tools in lung cancer", 5(3):281-91 (2011).
Royston, "An extension of Shapiro and Wilk's W test for normality to large samples", Applied Statistics, 31:115-24 (1982).
Royston, "Model-based screening by risk with application to Down's syndrome", Statistics in Medicine, 11(2)257-68 (1992).
St. Clair, "Copy Number Variation and Schizophrenia", Schizophr. Bull., 35(1):9-12 (2009).
Savas, "Useful genetic variation databases for oncologists investigating the genetic basis of variable treatment response and survival in cancer", Acta Oncol., 49(8):1217-26 (2010).
Schuster, et al, "Next-generation sequencing transforms today's biology", Nat. Methods, 5:16-18 (2008).
Scriven, et al., "Robertsonian translocations—reproductive reisks and indications for preimplantation genetic diagnosis", Human Reproduction, 16(11):2267-73 (2001).
Sebat, et al., "Strong Association of De Novo Copy Number Mutations with Autism", Science, 316(5823):445-49 (2007).
Sehnert, et al., "Optimal detection of fetal chromosomal abnormalities by massively parallel DNA sequencing of cell-free fetal DNA from maternal blood", Clin Chem, 57: 1042-49 (2011).
Shamash, et al., "Preimplantation genetic haplotyping a new application for diagnosis of translocation carrier's embryo—preliminary observations of two robertsonian translocation carrier families", J. Assist. Reprod. Genet., 28:77-83 (2011).
Simpson and Elias, "Isolating Fetal Cells from Maternal Blood", JAMA, 270(19):2357-61 (1993).
Simpson, "Is Cell-Free Fetal DNA from Maternal Blood Finally Ready for Prime Time?", Obst & Gynecol., 119(5):1-3 (2012).
Snyder, et al., "Universal noninvasive detection of solid organ transplant rejection", PNAS USA, 108(5):6229-34 (2011).
Sorenson, "Cancer Epidemiology, Biomarkers and Prevention", Cancer Epidem. Biomarkers Prev., 3_67-71 (1994).
Stroun, et al., "Neoplastic Characteristics of the DNA Found in the Plasma of Cancer Patients", Oncology, 46: 318-322 (1989).
Stroun, et al., "Isolation and Characterization of DNA from the Plasma of Cancer Patients", Eur. J. Cancer Clin. Oncol., 23(6) 707-12 (1987).
Sullivan, et al., "Evidence for Structural Heterogeneity from Molecular Cytogenetic Analysis of Dicentric Robertsonian Translocations", Am. J. Hum. Genet., 59:167-75 (1996).
Tong, et al., "Noninvasive prenatal detection of fetal trisomy 18 by epigenetic allelic ratio analysis in maternal plasma: theoretical and empirical considerations", Clin Chem, 52:2194-202 (2006).
Tsui, et al., "Systematic microarray-based identification of placental mRNA in maternal plasma: towards noninvasive prenatal gene expression profiling", J. Med Genet, 41:461-67 (2004).

(56) References Cited

OTHER PUBLICATIONS

Tsui, et al., "Noninvasive prenatal diagnosis of hemophilia by microfluidics digital PCR analysis of maternal plasma DNA", Blood, 117:3684=91 (2011).
Vogelstein, et al., "Digital PCR", PNAS USA, 96:9236-41 (1999).
Wachtel, et al., "Fetal cells in the maternal circulation: Isolation by multiparameter flow cytometry and confirmation by polymerase chain reaction", Human Reprod., 6(10):1466-69 (1991).
Wald, et al., "Maternal serum screening for Down's syndrome in early pregnancy", BMJ, 297:883-87 (1988).
Wald, et al., "Antenatal maternal serum screening for Down's syndrome: results of a demonstration project", BMJ, 305(6850):391-94 (1992).
Wang, et al., "PennCNV: An integrated hidden Markov model designed for high-resolution copy number variation detection in whole-genome SNP genotyping data", Genome Res., 17:1665-74 (2007).
Ward, et al. "Reactivities of serotyping monoclonal antibodies with culture-adapted human rotaviruses", J. Clin. Microbiol. 29(3):422-25 (1991).
Winsor, et al., "Maternal Cell Contamination in Uncultured Amniotic Fluid", Prenatal Diagnosis, 16:49-54 (1996).
Wu and Wallace, "The ligation amplification reaction (LAR)—Amplification of specific DNA sequences using sequential rounds of template-dependent ligation", Genomics, 4:560-69 (1989).
Young and Davis, "Efficient isolation of genes by using antibody probes", PNAS 80:1194-98 (1983).
Lapair, et al., "Cell-Free DNA in Amniotic Fluid: Unique Fragmentation Signatures in Euploid and Aneuploid Fetuses", Clinical Chem., 53(3):405-11 (2007).
Office Action Received on May 10, 2012 for U.S. Appl. No. 13/293,419.
Search Report Received on Jan. 20, 2012 for (PCT/US2012/21955).
Search Report Received on May 2, 2012 for PCT/US2011/046935).
earch Report Received on May 10, 2012 for (PCT/US2012/026754).
Search Report Received on May 11, 2012 for (PCT/US2012/022261).
Ashoor, et al., "Chromosome-selective sequencing of maternal plasma cell-free DNA for first-trimester detection of trisomy 21 and trisomy 18", Am. J. of Obstet. Gynecol., (2012), doi: 10.1016/j.ajog.2012.01.029.
Bodurtha and Strauss, "Genomics and Prenatal Care", New Eng. J. of Medicine, 366:64-73 (2012).
Chiu, et al., "Noninvasive prenatal diagnosis of fetal chromosomal aneuploidy by massively parallel genomic sequencing of DNA in maternal plasma", PNAS USA 105:20458-63 (2008) Supporting Information.
Sparks, et al., "Noninvasive prenatal detection and selective analysis of cell-free DNA obtained from maternal blood: evaluation for trisomy 21 and trisomy 18", Am. J. Obstet. Gynecol., (2012), 206:319.e1-9.
Sparks, et al., "Selective analysis of cell-free DNA in maternal blood for evaluation of fetal trisomy", Prenatal Diagnosis, 32:1-7 (2012).
Sparks, et al., "Non-invasive Prenatal Detection and Selective Analysis of Cell-free DNA Obtained from Maternal Blood: Evaluation for Trisomy 21 and Trisomy 18", Am. J. Obstet. Gynecol., (2012), doi:10.1016/j.ajog.2012.01.030.
Search Report Received on Aug. 13, 2012 for (PCT/US2011/046976).
Office Action Received on Jul. 5, 2012 for U.S. Appl. No. 13/013,732.
Enders, et al., "Fetal morbidity and mortality after acute human parvovirus B19 infection in pregnancy: prospective evaluation of 1018 cases", Prenatal Diagnosis, 24:513-18 (2004).
Smith, et al., "Quantitative phenotyping via deep barcode sequencing", Genome Res., 19:1836-42 (2009).
Van Opstal, et al., "Rapdi aneuploidy detection with multiplex ligation-dependent probe amplification: a prospective study of 4000 amniotice fluid samples", Eur. J. of Hum. Genetics, 17:112-21 (2009).

Xie and Tammi, "CNV-seq, a new method to detect copy number variation using high throughput sequencing", BMC Bioinformatics, 10:80 (2008), doi 10.1186/1471-2105-10-80, p. 1-9.
Office Action Received on Apr. 15, 2013 for U.S. Appl. No. 13/356,133 (inventor A. Oliphant, filed Jan. 23, 2012), entire document.
Office Action Received on May 17, 2013 for U.S. Appl. No. 13/356,575 (inventor A. Oliphant, filed Jan. 23, 2012), entire document.
Office Action Received on Apr. 5, 2013 for U.S. Appl. No. 13/689,206 (inventor A. Oliphant, filed Nov. 39, 2012).
Final Office Action Received on Jul. 8, 2013 for U.S. Appl. No. 13/689,206 (inventor A. Oliphant, filed Nov. 39, 2012), entire document.
Office Action Received on Jul. 5, 2012 for U.S. Appl. No. 13/013,732 (inventor A. Oliphant, filed Jun. 25, 2011).
Office Action Received on Dec. 7, 2012 for U.S. Appl. No. 13/013,732 (inventor A. Oliphant, filed Jun. 25, 2011), entire document.
Office Action Received on Apr. 11, 2013 for U.S. Appl. No. 13/013,732 (inventor A. Oliphant, filed Jun. 25, 2011), entire document.
Office Action Received on May 13, 2013 for U.S. Appl. No. 13/407,978 (inventor K. Song, filed Feb. 29, 2012), entire document.
Office Action Received on Jul. 8, 2013 for U.S. Appl. No. 13/205,490 (inventor A. Sparks, filed Aug. 8, 2011), entire document.
Office Action Received on Mar. 28, 2013 for U.S. Appl. No. 13/687169 (inventor A. Sparks, filed Nov. 28, 2012), entire document.
Office Action Received on Feb. 28, 2013 for U.S. Appl. No. 13/205,570 (inventor A. Sparks, filed Aug. 8, 2011), entire document.
Office Action Received on Mar. 14, 2013 for U.S. Appl. No. 13/687,025 (inventor A. Sparks, filed Nov. 28, 2012), entire document.
Office Action Received on May 10, 2012 for U.S. Appl. No. 13/293,419 (inventor A. Sparks, filed Nov. 10, 2011), entire document.
Office Action Received on Aug. 22, 2012 for U.S. Appl. No. 13/293,419 (inventor A. Sparks, filed Nov. 10, 2011), entire document.
Final Office Action Received on Oct. 12, 2012 for U.S. Appl. No. 13/293,419 (inventor A. Sparks, filed Nov. 10, 2011), entire document.
Advisory Action Received on Jan. 29, 2013 for U.S. Appl. No. 13/293,419 (inventor A. Sparks, filed Nov. 10, 2011), entire document.
Office Action Received on Feb. 28, 2013 for U.S. Appl. No. 13/245,133 (inventor A. Oliphant, filed Sep. 26, 2011), entire document.
Office Action Received on Jun. 13, 2013 for U.S. Appl. No. 13/316,154 (inventor A. Oliphant, filed Dec. 9, 2011), entire document.
Office Action Received on Jun. 13, 2013 for U.S. Appl. No. 13/338,963 (inventor A. Oliphant, filed Dec. 28, 2011), entire document.
Office Action Received on Feb. 15, 2013 for U.S. Appl. No. 13/689,417 (inventor A. Oliphant, filed Nov. 29, 2012), entire document.
Search Report Received on Feb. 21, 2013 for (PCT/US2011/046963), entire document.
Search Report Received on Apr. 19, 2013 for (PCT/US2012/70177), entire document.
Abadia-Molina, et al., "Immune phenotype and cytotoxic activity of lymploycytes from human term decidua against trophoblast", J. of Reproductive Immunology, n31:109-23 (1996).
Anker, et al., "Spontaneous Release of DNA by Human Blood Lymphocytes as Shown in an in Vitro System", Cancer Research, 35:2375-82 (1975).
Anker, et al., "K-ras Mutations are found in DNA extreacted from the plasma of patients with colorectal cancer," Gastroenterology, 112:1114-20 (1997).
Anker, et al., Information carried by the DNA release by antigen-stimulated lymphocytes:, Immunology, 37:753-63 (1979).

(56) References Cited

OTHER PUBLICATIONS

Ashoor, et al., Fetal Fraction in Maternal Plasma Cell-Free DNA at 11-13 Weeks' Gestation: Effect of Maternal and Fetal Factors, Fetal Dian Ther DOI:10.1159/000337373 (Pub'd online May 4, 2012).

Batzer and Deininger, "ALU Repeats and Human Genomic Diversity", Nature, 3:370-79 (2002).

Beard, "Embryological Aspects and Etiology of Carcinoma", The Lancet, Jun. 21, 1902, pp. 1758-1761.

Belokhvostov, et al., "Changes in the Fractional Composition of the Nucleic Acids in Blood Serum upon Rediation Damage Early Stage Abnormalities Following Gamma-Irradiation of Rats", Tsitologiia (Cytology) 1986.

Bradstock, et al., "Functional and phenotypic assessment of neonatal human leucocytes expressing natural killer cell-associated antigen", Immunology and Cell Biology (71:535-42 (1993).

Campbell, et al., "Subclonal phylogenetic structions in cancer revealed by ultra-deep sequencing", PNAS, 105(35):13081-86 (2008).

Cicuttini and Boyd, "Hemopoietic and Lymphoid Progenitro Cells in Human Umbilical Cord Blood", Developmental Immunology, 4:1-11 (1994).

Datta, et al., "Sensitive Detection of Occult Breast Cancer by the Reverse-Transcriptase Polymerase Chain Reaction", J. of Clinical Oncology, 12(3): 475-82 (1994).

Dennin, "DNA of Free and Complexed Origin in Human Plasma: Concentration and Length Distribution", Klin. Wochenschr., 57:451-56 (1979).

Fisher, et al., "Genetic evidence that placental site trophoblastic tumours can originate from a hydatidiform mole or a normal conceptus", Br. J. Cancer, 65:355-358 (1992).

Fournie, et al., "Plasma DNA as Cell Death Marker in Elderly Patients", Gerontology, 39:215-221 (1993).

Geifman-Holzman, et al., "Fetal RhD genotyping in fetal cells flow sorted from maternal blood", Am. J. Obstet. Gynecol., 174(3):818-22 (1996).

Ghossein, et al.. "Detection of Circulating Tumor Cells in Patients With Localized and Metastatic Prostatic Carcinoma Clinical Implications", J. of Clin. Oncology, 13(5):1995-200 (1995).

Green, et al., "Gestational Trophoblastic Disease: A Spectrum of Radiologic Diagnosis", Radiographics, 16(6):1371-84 (1996).

Gribben, et al., "Detection of Residual Lymphoma Cells by Polymerase Chain Reaction in Peripheral Blood is Significantly Less Predictive for Relapse Than Detection in Bone Marrow", Blood, 83(12):3800-07 (1994).

Hardingham, et al., "Detection of Circulating Tumor Cells in Colorectal Cancer by Immunogead-PCR is a Sensitive Prognostic marker for Relapse of Disease", Molecular Medicine, 1(7):789-94 (1995).

Heid, et al., "Real Time Quantitative PCR", Genome Res., 6:986-94 (1996).

Ho, et al., "Activation Status of T and NK Cells in the Endometrium Throughout Menstrual Cycle and Normal and Abnormal Early Pregnancy", Human Immunology, 49:130-36 (1996).

Hoon, et al., "Detection of Occult Melanoma Cells in Blood With a Multiple-Marker Polymerase Chain Reaction Assay", J. of Clinical Oncology, 13(8):2109-116 (1995).

International Human Genome Sequencing Consortium, "Initial sequencing and analysis of the human genome", Nature, 409:860-921 (2001).

Kazakov, et al., "Extracellular DNA in the Blood of Pregnant Women", Tsitologiia (Cytology), 37(3):232-37 (1995).

Kogan, et al, "An improved method for prenatal diagnosis of genetic diseases by analysis of amplified DNA sequences", New England J. of Medicine, 317(6):985-90 (1987).

Krebs, et al., "The Unitarian or Trophoblastic Thesis of Cancer" Medical Record, 163:149-74 (Jul. 1950).

Margulies, et al., "Genome sequencing in microfabricated high-density picolitre reactors", Nature, 437(15):376-80 and errata (2005).

Mikhaylov, et al., "Changes in the quantity and synthesis of DNA in the nuclei of large decidual cells of rats in the course of their differentiation", Tsitologiia (Cytology),41(6):677-83, 1989.

Mikhaylov, et al., "Synthesis and content of DNA in human decidual cells at various stages of differentiation according to flow cytometry analysis", Tsitologiia (Cytology), 34(6):67-72 (1992).

Moffet-King, et al., "Natural Killer Cells and Pregnancy", Nature Reviews Immunology, 2002(2):656-63.

Moreno and Gomella, "Circulating Prostate Cancer Cells Detected by Reverse Transcription-Polymerase Chain Reaction (RT-PCR: What do they mean?", Cancer Control Journal, 5(6) 1998.

Mulcahy, et al., "Plasma DNA K-rase Mutations in Patients with Gastrointestinal Malignancies," Annals New York Academy of Sciences, 25-28, 2000.

Nelson, et al., "Alu polymerase chain reaction: A method for rapid isolation of human-specific sequence from complex DNA sources, " PNAS USA, 86:6686-90 (1989).

Paolella, et al., "The Alu family repeat promoter has a tRNA-like bipartite structure", EMBO J., 2(5):691-96 (1983).

Oei, et al., "Clusters of regulatory signals for RNA polymerase II transcription associated with Alu family repeats and CpG islands in human promoters", Genomics, 83:873-82 (2004).

Robbins, et al., *Pathologic Basis of Disease $5^{nd}$ Ed.*, Chapter 23, pp. 1071-88 (1994).

Ronaghi, et al., "A Sequencing Method Based on Real_Time Pyrophosphate", Science, 281:363-65 (1998).

Saiki, et al., "Primer-directed Enzymatic Amplification of DNA with a Thermostable DNA Polymerase", Science, 239:487-91 (1987).

Schallhammer, et al., "Phenotypic comparison of natural killer cells from peripheral blood and from early pregnancy decidua", Early Pregnancy: Biology and Medicine, 3:15-22 (1997).

Schroder, et al., "Transplacental passage of blood cells", J. of Medical Genetics, 12:230-42 (1974).

Shapiro, et al., "Determination of Circulating DNA Levels in Patients with Benign or Malignant Gastrointestinal Disease", Cancer, 51:2116-20 (1983).

Shendure, et al., "Accurate Multiplex Polony Sequencing of an Evolved Bacterial Genome", Science, 309:1728-32 (2005).

Simpson, et al., "Isolating Fetal Cells in Maternal Circulation for Prenatal Diagnosis", Prenatal Diagnosis, 14:1229-42 (1994).

Smith, et al., "Detection of melanoma cells in peripheral blood by means of reverse transcriptase and polymerase chain reaction", The Lancet, 338:1227-29 (1991).

Smith, et al.. "Placental apoptosis in normal human pregnancy", Am. J. Obstet. Gynecol, Jul. 1997, pp. 57-65.

Sorenson, et al., "Soluble normal and mutated DNA sequences from single-copy genes in human blood", Cancer Epidemmiol. Biomarkers, 3:64-71 (1994).

Stroun, et al., "Circulating Nulceic Acids in Higher Organisms", Rev. Cytol. 51:1-48 (1977).

Stroun, et al., The Origin and Mechanism of Circulating DNA, Annals New York Academy of Sciences, 906:161-68 (2000).

Tagle, et al., "An optimized Alu-PCR primer pair for human-specific amplification of YACs and somatic cells hybrids", Human Molecular Genetics, 1(2):121-22 (1992).

Agostini, et al., "Circulating cell-free DNA: a promising marker of pathologic tumor response in rectal cancer patients receiving pre-operative chemotherapy", Ann. Surg. Oncol., 18(9):2461-68 (2011).

Alexandrov, et al., "Definition of a new alpha satellite suprachromosomal family characterized by monomeric organization", Nucleic Acids Research, 21(9):2209-15 (1003).

Arnheim, et al., "Molecular evidence for genetic exchanges among ribosomal genes on nonhomologous chromosomes in man and apes", PNAS USA, 77(12):7323-27 (1980).

Bandyopadhyay, et al, "Identification and characterization of satellite III subfamilies to the acrocentric chromosomes", Chromosome Research, 9:223-33 (2001).

Bianchi, "Prenatal diagnosis by analysis of fetal cells in maternal blood", J. of Pediatrics, 127(6):847-56 (1995).

Bianchi, "Isolation of fetal DNA from nucleated erythrocytes in maternal blood", PNAS USA, 87:3279-83 (1990).

(56) References Cited

OTHER PUBLICATIONS

Bianchi, "PCR Quantitation of Fetal Cells in Maternal Blood in Normal and Aneuploid Pregnancies", Am J. Hum. Genet., 61:822-29 (1997).
Biran, "On the Oncodevelopmental Rold of Human Imprinted Genes", 43:119-23 (1994).
Blaschke and Rappold, "The Pseudoautosomal regions, SHOX and disease", Curr. Opin. Gene. Dev., 16(3):23-29 (2006).
Bombard, et al., "Fetal RHD genotype detection from circulating cell-free DNA in maternal plasma in non-sensitized RhD negative women", Prenat Diagn, 31:802-08 (2011).
Camaschella, et al., "Prenatal Diagnosis of Fetal Hemoglobin Lepore-Boston Disease on Maternal Peripheral Blood", Blood, 75(11):2102-06 (1990).
Cappuzzo, et al., "Epidermal growth factor receptor gene and protein and gefitinib sensitivity in non-small-cell lung cancer", J. Natl Cancer Inst., 97(9):643-55 (2005).
Chen, et al., "Microsatellite alterations in plasma DNA of small cell lung cancer patients", Nature Medicine, 2(9):1033-35 (1996).
Chen, et al., "Noninvasive prenatal diagnosis of fetal trisomy 18 and trisomy 13 by maternal plasma DNA sequencing", PLos One, 6:e21791 (2011).
Chim, et al., "Detection of the placental epigenetic signature of the *maspin* gene in maternal plasma", PNAS USA, 102(41):14753-58 (2005).
Chiu, et al, "Effects of Blood-Processing Protocols on Fetal and Total DNA Quantification in Maternal Plasma", Clin. Chem., 47(9):1607-1613 (2001).
Chiu, et al., "Maternal plasma DNA analysis with massively parallel sequencing by ligation for noninvasive prenatal diagnosis of trisomy 21", 56:459-63 (2010).
Chiu, et al, "Noninvasive prenatal diagnosis of fetal chromosomal aneuploidy by massively parallel genomic sequencing of DNA in maternal plasma", PNAS USA 105:20458-63 (2008).
Chiu and Lo, "Non-invasive prenatal diagnosis by fetal nucleic acid analysis in maternal plasma: the coming of age", Semin. Fetal Neonatal Med., 16(2):88-93 (2011).
Chiu, et al., "Non-invasive prenatal assessment of trisomy 21 by multiplexed maternal plasma DNA sequencing: large scale validity study", Br Med J. 342:c7401 (2011).
Cirigiliano, et al., "Clinical application of multiplex quantitative fluorescent polymerase chain reaction QF-PCR for the repaid prenatal detection of common chromosome aneuploidies", Molecular Human Reproduction, 7(10):1001-06 (2001).
Cirigiliano, et al., "Rapid prenatal diagnosis of common chromosome aneuploidies by QF-PCR, results of 9 years of clinical experience", Prenatal diagnosis, 29:40-49 (2009).
Choo, et al., "A homologous subfamily of satellite III DNA on human chromosomes 14 and 22", Nucleic Acids Research, 18(19):5641-47 (1990).
Choo, et al., "A Chromosome 14-specific Human Satellite III DNA Subfamily That Shows Variable Presence on Different Chromosomes 14", Am J. Hum. Genet., 50:706-16 (1992).
Chromosome 14 map, 2001.
Chu, et al., "A novel approach toward the challenge of accurately quantifying fetal DNA in maternal plasma", Prenat. Diag., 30:1226-29 (2010).
Ciccodicola, et al., "Differentially regulated and evolved genes in the fully sequences Xq/Yq pseudoautosomal region", Hum. Mol. Genet., 9(3):395-401 (2000).
Cockwell, et al., "Distribution of the D15A1 copy number polymorphism", European J. of Hum. Genet., 15:441-45 (2007).

Conover, Practical Nonparametric Statistics, pp. 295-301 (John Wiley & Sons, NY)(1971).
Costa, et al., "New strategy for prenatal diagnosis of X-linked disorders", N. Engl J. Med., 346:1502 (2002).
Dear, et al., "A High-Resolution Metric HAPPY Map of Human Chromosome 14" Genmoics, 48 232-41 (1998).
Dhallan, et al., "A non-invasive test for prenatal diagnosis based on fetal DNA present in maternal blood: a preliminary study", Lancet, 369(9560):474-81 (2007).
Dobrzycka, et al., "Circulating free DNA and p53 antibodies in plasma of patients with ovarian epithelial cancers", Annals of Oncology, 22:1133-40 (2011).
Dobrzycka, et al., "Prognostic significance of VEGF and its receptors in endometrioid endometrial cancer", Ginekol Pol. 81(6):422-25 (2010).
Duan, et al., "PstSNP-HapMap3: a database of SNPs with high population differentiation for HapMap3", Bioinformation, 3(3):139-41 (2008).
Earle, et al., "Identification of DNA Sequences Flanking the Breakpoin of Human t(14q21q) Robertsonian Translocations", Am J. Hum Genet., 50:717-24 (1992).
Enrich, et al., "Noninvasive detection of fetal trisomy 21 by sequencing of fetal DNA in maternal blood: a study in a clinical setting", Am J. Obstet Gynecol, 2011:204:205 e1-11 (2011).
Fan, et al., "Noninvasive diagnosis of fetal aneuploidy by shotgun sequencing DNA from maternal blood", PNAS USA, 105(42):16266-71 (2008).
Fan, et al., "Analysis of the Size Distributions of Fetal and Maternal Cell-Free DNA by Paired-End Sequencing", Clin. Chem., 56(8):1279-80 (2010).
Fan, et al., "Sensitivity of noninvasive prenatal detection of fetal aneuploidy from maternal plasma using shotgun sequencing is limited only by counting statistics", PLoS One, 5:e10439 (2010).
Fejgin, et al., "Fetal cells in the uterine cervix: a source for early non-invasive prenatal diagnosis", Prenat. Diag., 21:619-21 (2001).
Finning, et al., "Effect of high throughput RHD typing of fetal DNA in maternal plasma on use of anti-RhD immunoglobulin in RhD negative pregnant women: prospective feasibility study", Br Med J., 336:816-18 (2008).
Fisher, et al., "Genetic evidence that placental site trophoblastic tumours can originate from a hydatidiform mole or a normal conceptus", Br. J. Cancer, 65:355-58 (1992).
Fowke, Genetic analysis of human DNA recovered from minute amounts of serum and plasma, J. of Immunol. Meth., 180:45-51 (1995).
Gold, "Cancer and Pregnancy: Parallels in Growth, Invasion, and Immune Modulation and Implicationsa for Cancer Therapeutic Agents", Mayo Clin. Proc., 84(11):985-1000 (2009).
Gosden, et al., "Satellite DNA Sequences in the Human Acrocentric Chromosomes: Information from Translocations and Heteromorphisms", Am. J. Hum. Genet., 33:243-51 (1981).
Greeley, et al., "Get ready for the flood of fetal gene screening", Nature, 469:289-91 (2011).
Guatelli, et al., "Isothermal, in vitro amplification of nucleic acids by a multienzyme reaction modeled after retroviral replication", PNAS USA, 87(5):1874- (1990).
Han, et al, "Molecular Chytogenetic Characterization of 17 rob(13q14q) Robertsonian Translocations by FISH, Narrowing the Region Containing the Breakpoints", Am J. Hum. Genet., 55:960-67 (1994).
Harrell, Regression modeling strategies, §§9.2.2 and 1.10.5 (Springer Vertag)(2001).

\* cited by examiner

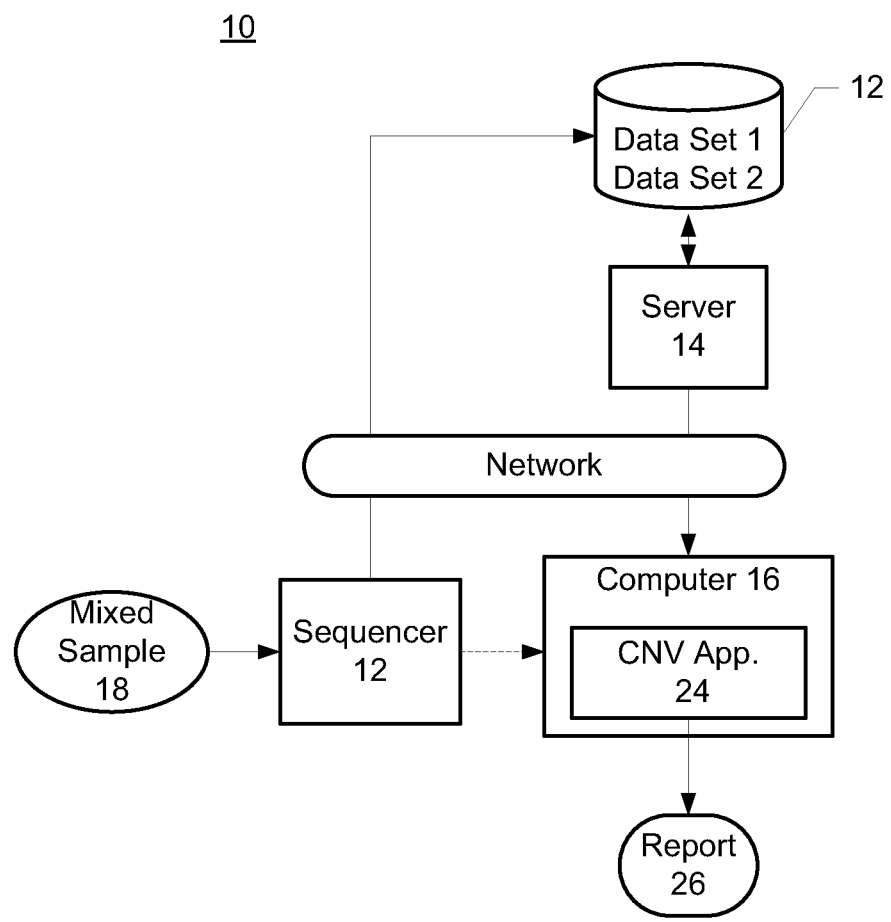

DETERMINATION OF COPY NUMBER VARIATIONS USING BINOMIAL PROBABILITY CALCULATIONS

CROSS-REFERENCE TO RELATED APPLICATIONS

The present application claims priority to U.S. Ser. No. 61/531,738, filed Sep. 7, 2011, which is herein incorporated by reference.

FIELD OF THE INVENTION

This invention relates to processes using binomials for providing best fit probabilities for data sets.

BACKGROUND OF THE INVENTION

In the following discussion certain articles and processes will be described for background and introductory purposes. Nothing contained herein is to be construed as an "admission" of prior art. Applicant expressly reserves the right to demonstrate, where appropriate, that the articles and processes referenced herein do not constitute prior art under the applicable statutory provisions.

Recent advances in diagnostics have focused on less invasive mechanisms for determining disease risk, presence and prognosis. Diagnostic processes for determining genetic anomalies have become standard techniques for identifying specific diseases and disorders, as well as providing valuable information on disease source and treatment options.

Characterization of cell free nucleic acids in biological samples such as blood and plasma allows for less invasive techniques such as blood extraction to be used in making clinical decisions. For example, cell free DNA from malignant solid tumors has been found in the peripheral blood of cancer patients; individuals who have undergone organ transplantation have cell free DNA from the transplanted organ present in their bloodstream; and cell-free fetal DNA and RNA have been found in the blood and plasma of pregnant women. In addition, detection of nucleic acids from infectious organisms, such as viral or bacterial pathogens, provides important diagnostic and prognostic indicators.

However, the sensitivity of such testing is often dependent upon the identification of the amount of nucleic acid from the different sources, and in particular identification of a low level of nucleic acid from one source against a background of a much higher level of nucleic acids from a second source (e.g., fetal DNA in maternal plasma or viral nucleic acids in a patient sample). Determining the contribution of the minor nucleic acid species to the total nucleic acids present in the biological sample permits more accurate statistical interpretation of the resulting data.

In the case of copy number variants or aneuploidies, the portion of the chromosome with the copy number variant or the aneuploid chromosome may be genotypically identical to the background maternal DNA, hence fetal inheritance of an extra chromosome or portion thereof cannot be established merely by detecting the presence of nucleic acid sequences from the extra chromosome in the maternal sample.

There is thus a need for processes for calculating copy number variation (CNV) in one or more genomic regions in a biological sample using information on contribution of nucleic acids in the sample.

SUMMARY OF THE INVENTION

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description including those aspects illustrated in the accompanying drawings and defined in the appended claims.

The present invention relates to processes for identifying copy number variation (CNV) in one or more genomic regions. The methods of the invention comprise 1) calculating the estimated contribution of a first source and a second source in a mixed sample; and 2) calculating CNV for one or more genomic regions in the second source based on frequency data for the genomic regions and estimated source contribution.

The processes of the invention utilize binomial probability distributions of distinguishing regions in informative loci to determine the relative contribution of the loci from different sources in a mixed sample. CNV for a genomic region can be determined based on a comparison of the source contribution in a mixed sample to empirical copy numbers for a selected locus from a source in the mixed sample. The source contribution used for comparison is preferably the source for which the CNV is being determined.

CNV can also be based on the frequency data of the selected loci from a reference mixed sample having a source contribution substantially the same as the source contribution of the mixed sample from which the empirical copy numbers for a selected locus are obtained.

The processes and systems of the invention allow identification of CNV for larger genomic regions (e.g., genomic regions encompassing multiple loci). This can be accomplished using two or more loci that are present in the genomic region or associated with the genomic region. Information on the frequency of a set of loci can determine not only the CNV for a particular genomic region, but in certain embodiments it can also determine the relative boundaries of the region by selection of particular loci in a set present in or around such boundaries.

In a first implementation, the invention provides a process for estimating the CNV of a selected locus by 1) calculating the source contribution of a first source and/or a second source in a mixed sample using frequency data derived from two or more informative loci; and 2) identifying a CNV for one or more genomic regions in the second source by comparing copy number of the genomic region from the second source in the mixed sample to the source contribution in the mixed sample. The source contribution used for comparison is preferably the contribution of the second source. In a preferred embodiment, the source contribution is determined through identification of distinguishing regions on copies of the informative loci in the cell free nucleic acids in the mixed sample.

In a specific aspect, the source contribution in the mixed sample is calculated by sequencing one or more distinguishing regions of informative loci copies present in a mixed sample and measuring the frequency of the copies present in the mixed sample. The frequency of loci can be measured as "counts", i.e., the number of the particular alleles of the informative loci identified in the mixed sample. The binomial distribution calculation is carried out using the counts of the alleles of the informative loci from the first source and the second source in a mixed sample. An estimate of the contribution of the first source nucleic acids and/or the second source nucleic acids can thus be calculated from these frequency data sets. The counts can be based on raw data, or the counts may be normalized to take into account experimental variation.

The required number of informative loci for an accurate determination of copy number variation in a genomic region depends upon a number of variables, as will be apparent to one skilled in the art upon reading the present disclosure. In general, enough loci need to be used to have statistical power to detect copy number variants of one or more genomic regions as compared to the source contribution of the second source. The variables that affect statistical power include source contribution of the different sources in the mixed sample and variation of copy numbers between informative loci used to determine source contribution in a mixed sample. In a preferred aspect, the selected locus for which CNV is being interrogated is not used as an informative locus for the calculation of source contribution in the mixed sample, although in certain aspects the selected locus can be included in the frequency data used for this calculation.

In certain aspects, copy number variation for a genomic region can be determined by directly comparing the frequency of the locus or loci in a mixed sample to the source contribution in the mixed sample, and preferably to the contribution of the second source in the mixed sample. The frequency of the one or more loci can be determined through various means known to those skilled in the art. In certain embodiments, a single empirical assay is used to determine both source contribution and the copy number of one or more loci in the mixed sample. Copy number variation can then be determined based on mathematical modeling of the different frequency data obtained from the results of the single assay, as described in more detail herein. In other aspects, the copy number of the one or more genomic regions can be determined using a separate assay on the mixed sample, and the information input for calculation of the CNV of the loci in the mixed sample.

In a preferred embodiment, the copy number variation is determined for a larger genomic region in a mixed sample using a comparative of two or more, and preferably five or more, selected loci in a mixed sample. The CNV for the genomic region is preferably determined using a statistical method such as Markov modeling. A Markov model is a stochastic model that assumes the Markov property, i.e., the conditional probability distribution of future states of the process, given the present state and the past states, depend only upon the present state. In the Markov process, the past is irrelevant because it does not affect how the current state was obtained. Generally, this assumption enables reasoning and computation with the model that would otherwise be intractable. For exemplary modeling, see e.g., Wang K., *Genome Res.* 2007 17: 1665-1674. In such embodiments, the copy number of loci within or associated with a genomic section in a mixed sample are measured empirically, and compared to the source contribution in the mixed sample. Thus, the invention provides a process for utilizing data sets of counts for one or more distinguishing regions of two or more informative loci to derive source contribution from two or more sources of cell free nucleic acids within a mixed sample.

In one specific aspect, the mixed sample is a maternal sample comprising maternal and fetal cell free nucleic acids. The source contribution is derived using counts of maternal and fetal cell free nucleic acids from cell free DNA ("cfDNA") in the mixed sample.

In one implementation, the invention provides a computer-implemented process for estimating the CNV for one or more genomic regions from a single source in a mixed sample, wherein at least one processor coupled to a memory executes a software component that performs the process comprising: accessing by the software component a first data set comprising frequency data for two or more informative loci from a first source; accessing by the software component a second data set comprising frequency data for two or more informative loci from a second source; calculating source contribution based on a binomial distribution of distinguishing regions from first and second data sets; and calculating the CNV for a genomic region by comparison of the frequency data of the genomic region in the mixed sample to the source contribution. Preferably, the CNV of a genomic region from the second source is calculated by comparing the relative frequency of the selected locus to source contribution of the second source in the mixed sample.

In certain embodiments using a set of loci to determine the CNV of a larger genomic region in a single source, the CNV is calculated using a binomial probability calculation of loci copy numbers in the mixed samples. The frequency of a first locus that is putatively normal in the mixed sample can be compared to the frequency of a second locus interrogated for CNV in the mixed sample, and the likelihood that the second locus displays a copy number variation can be based on the loci comparison as informed by the contribution of the source to the mixed sample.

In the various embodiments, the copy number of a genomic region for which CNV is calculated is introduced to the processor as a separate data set from the information used to calculate source contribution. In other embodiments, the copy number of a genomic region is a subset of the frequency data of the first and/or second data set used for calculation of source contribution, and the information is drawn from this data set for the calculation of CNV for the selected locus.

In a preferred implementation of the process and the systems of the invention, the calculations for determination of source contribution and/or for determination of CNV are performed using an algorithm that calculates a binomial probability distribution based on the frequency data from the first and/or second data sets. The contribution of the loci from the first and second sources in a mixed sample can be estimated by calculating the maximum likelihood estimate based on the frequency of the informative loci from the first source and the second source. In a more specific implementation, the maximum likelihood estimate is modeled by the equation:

$$\text{Binomial}(A, B, p) = \frac{(A+B)!}{A!B!} p^A (1-p)^B$$

wherein A is the quantity of copies of an informative locus from the second source, B is the quantity of copies of an informative locus from the first source, and p is the maximum likelihood estimate for the binomial distribution with quantities A and B.

The probability p corresponding to the maximum likelihood estimate is calculated within a machine environment using an optimization algorithm. Examples of optimization algorithms include, but are not limited to, gradient descent, simulated annealing, and evolutionary algorithms.

Preferably, the frequency data sets from the first and second sources are used to calculate source contribution using a first binomial distribution, and a subset of the frequency data is used to calculate CNV for one or more selected loci using a second binomial distribution calculation. The frequency data used for the CNV may or may not distinguish counts for a locus based on locus source. Thus, in some aspects the CNV is detected using total counts of one or more loci from a mixed sample without regard as to the source of the locus in the mixed sample.

In one aspect, the invention provides processes for estimating CNV of one or more genomic regions using cell free nucleic acids in a mixed sample from an individual, the sample comprising cell free nucleic acids from both normal and putative genetically atypical cells. Such samples include, but are not limited to, samples comprising maternal and fetal cell free nucleic acids and samples that contain cell free nucleic acids from normal cells and cancerous cells.

In another aspect, the invention provides processes for estimating CNV of genomic regions in mixed samples comprising cell free nucleic acids from two or more different organisms in a sample from a single individual, e.g., mammalian nucleic acids from the host and nucleic acids from an infectious organism (e.g., bacterial, fungal or viral nucleic acids).

In yet another aspect, the invention provides processes for estimating CNV of genomic regions in mixed samples comprising cell free nucleic acids from a donor cell source and a host recipient cell source, e.g., cells from a transplant recipient and donor cells from the transplanted organ.

In another implementation the invention provides a computer-implemented process for calculating the copy number variation of a genomic region in a mixed sample, the process comprising: accessing by the software component a first data set comprising frequency data based on identification of one or more distinguishing regions of two or more informative loci from a first source in the sample; accessing by the software component a second data set comprising frequency data based on identification of one or more distinguishing regions of two or more informative loci from a second source in the sample; calculating the source contribution of cell free nucleic acids from the mixed sample; and calculating variation of the copy number of a genomic region in the sample by comparison of the copy number of the genomic region in the first source with the source contribution of cell free nucleic acids. Preferably, the copy number of the genomic region in the second source is compared with the source contribution of the second source in the mixed sample. The contribution of the cell free nucleic acids from the first and/or second sources are preferably calculated based on a binomial distribution of the counts of the distinguishing regions from the first and second data sets.

In a more specific implementation, the invention provides a computer-implemented process for calculating the contribution of cell free nucleic acids from a maternal source and a fetal source in a maternal sample, the system comprising: accessing by the software component a first data set comprising frequency data based on identification of one or more distinguishing regions of two or more informative loci from the maternal source in the sample; accessing by the software component a second data set comprising frequency data based on identification of one or more distinguishing regions in two or more informative loci of the fetal source in the sample; calculating the contribution of cell free nucleic acids in the maternal sample; and calculating variation of the copy number of the genomic region in the maternal sample by comparison of the copy number of a selected locus with the source contribution of cell free nucleic acids The source contribution of the cell free nucleic acids is preferably based on a binomial distribution of the counts of the distinguishing regions from the first and second data sets. Preferably, the CNV of a fetal nucleic acid is determined based on comparison of the locus frequency with the fetal source contribution in the mixed sample.

The calculation of the contribution of cell free nucleic acids in the mixed sample is preferably based on counts of the informative loci determined using a single assay system. In certain embodiments, the frequency of selected loci for the mixed sample is determined empirically using a separate assay from that used to determine the source contribution of the different sources in the mixed sample. In some embodiments, the copy number variation of the genomic region may be determined using reference frequencies of the selected loci for mixed samples with certain calculations of source contribution from the different sources.

In another implementation, the invention provides an executable software product stored on a computer-readable medium containing program instructions for determining CNV in a mixed sample, the program comprising instructions for: accessing by the software component a first data set comprising frequency data based on identification of distinguishing regions from copies of two or more informative loci from a first source; accessing by the software component a second data set comprising frequency data based on identification of distinguishing regions from copies of two or more informative loci from a second source; calculating the source contribution of cell free nucleic acids from the first source and/or second source based on a binomial distribution of the first and second data sets; and calculating variation of the copy number of one or more genomic regions in the sample by comparison of the copy number of one or more genomic regions with the contribution of cell free nucleic acids from the first source and/or second source.

In still another implementation, the invention provides an executable software product stored on a computer-readable medium containing program instructions for determining CNV for a genomic region in a maternal sample, the program comprising instructions for: accessing by the software component a first data set comprising frequency data based on identification of distinguishing regions from copies of two or more informative loci from a maternal source; accessing by the software component a second data set comprising frequency data based on identification of distinguishing regions from copies of two or more informative loci from a fetal source; calculating the source contribution of cell free nucleic acids from the maternal source and/or fetal source based on a binomial distribution of the first and second data sets; and calculating variation of the copy number of one or more genomic regions in the maternal sample by comparison of the copy number of the one or more genomic regions with the contribution of cell free nucleic acids from the maternal source and/or fetal source.

In another implementation, the invention provides an executable software product stored on a computer-readable medium containing program instructions for determining CNV for a genomic region in a mixed sample, the program comprising instructions for: accessing by the software component a first data set comprising frequency data based on identification of distinguishing regions from copies of two or more informative loci from a first source; accessing by the software component a second data set comprising frequency data based on identification of distinguishing regions from copies of two or more informative loci from a second source; calculating a source contribution of cell free nucleic acids from the first source and/or second source based on a binomial distribution of the first and second data sets; and calculating variation of the copy number of a genomic region by comparison of the copy number of a set of selected loci with the source contribution of cell free nucleic acids from the first source and/or second source.

In another implementation, the invention provides an executable software product stored on a computer-readable medium containing program instructions for determining CNV for a genomic region in a maternal sample, the program comprising instructions for: accessing by the software component a first data set comprising frequency data based on identification of distinguishing regions from copies of two or more informative loci from a maternal source; accessing by the software component a second data set comprising frequency data based on identification of distinguishing regions from copies of two or more informative loci from a fetal source; calculating the source contribution of cell free nucleic acids from the maternal source and/or fetal source based on a binomial distribution of the first and second data sets; and calculating variation of the copy number of a genomic region by comparison of the copy number of a set of selected loci with the source contribution of cell free nucleic acids from the maternal source and/or fetal source.

In yet another implementation, the invention provides a system comprising: a memory; a processor coupled to the memory; and a software component executed by the processor that is configured to access a first data set comprising frequency data for at least one distinguishing region from two or more informative loci from a first source in a mixed sample; input a second data set comprising frequency data for at least one distinguishing region from two or more informative loci from a second source in the mixed sample; calculate an estimated contribution of cell free nucleic acids from the first source and/or second source based on a binomial distribution of counts of the distinguishing regions from the first and second data sets; and calculate variation of the copy number of one or more genomic regions in the mixed sample by comparison of the copy number of the one or more selected loci with the estimated contribution of cell free nucleic acids in the mixed sample. In certain embodiments, the copy number of the selected loci corresponding to a genomic region is input as a separate data set. In other embodiments, the copy number of the selected loci corresponding to a genomic region is a subset of the first and/or second data set.

In a specific aspect the invention provides a computer software product including a non-transitory, computer-readable storage medium having fixed therein a sequence of instructions is executed by a computer direct performance of steps of: creating a first data set representing a quantity of copies of an informative locus from a first source in a mixed sample; creating a second data set representing a quantity of copies of informative locus from a second source in a mixed sample; calculating a source contribution of cell free nucleic acids based on a binomial distribution of distinguishing regions from first and second data sets; and determining the copy number variation of a genomic region in the mixed sample.

It is a feature of the invention that the calculation of source contribution of cell free nucleic acids can be optimized through summing the measured counts of informative loci, including the loci for which CNV is calculated.

It is another feature that the copy number of the genomic region may be empirically derived in the same assay used to determine source contribution in a mixed sample.

It is another feature that the copy number of the genomic region can be based on a reference number indicative of a likely frequency range of one or more selected loci corresponding to such genomic region for mixed samples such as those being analyzed.

These and other implementations, aspects, features and advantages will be provided in more detail as described herein.

DESCRIPTION OF THE FIGURES

FIG. 1 is a block diagram illustrating an exemplary system environment.

DETAILED DESCRIPTION

The exemplary embodiments set forth herein relate to estimating the source contribution of cell free nucleic acids in a mixed sample, and using this information in the determination of a CNV of one or more loci in a single source of a mixed sample. The following description is presented to enable one of ordinary skill in the art to make and use the invention and is provided in the context of a patent application and its requirements. Various modifications to the exemplary embodiments and the generic principles and features described herein will be readily apparent. The exemplary embodiments are mainly described in terms of particular processes and systems provided in particular implementations. However, the processes and systems will operate effectively in other implementations. Phrases such as "exemplary embodiment", "one embodiment" and "another embodiment" may refer to the same or different embodiments. The embodiments will be described with respect to systems and/or devices having certain components. However, the systems and/or devices may include more or less components than those shown, and variations in the arrangement and type of the components may be made without departing from the scope of the invention.

The exemplary embodiments will also be described in the context of particular processes having certain steps. However, the process and system operate effectively for other processes having different and/or additional steps and steps in different orders that are not inconsistent with the exemplary embodiments. Thus, the present invention is not intended to be limited to the embodiments shown, but is to be accorded the widest scope consistent with the principles and features described herein and as limited only by appended claims.

It should be noted that as used herein and in the appended claims, the singular forms "a," "and," and "the" include plural referents unless the context clearly dictates otherwise. Thus, for example, reference to "an informative locus" refers to one, more than one, or combinations of such loci, and reference to "a system" includes reference to equivalent steps and processes known to those skilled in the art, and so forth.

Unless expressly stated, the terms used herein are intended to have the plain and ordinary meaning as understood by those of ordinary skill in the art. The following definitions are intended to aid the reader in understanding the present invention, but are not intended to vary or otherwise limit the meaning of such terms unless specifically indicated. All publications mentioned herein are incorporated by reference for the purpose of describing and disclosing the formulations and processes that are described in the publication and which might be used in connection with the presently described invention.

DEFINITIONS

The terms used herein are intended to have the plain and ordinary meaning as understood by those of ordinary skill in the art. The following definitions are intended to aid the reader in understanding the present invention, but are not intended to vary or otherwise limit the meaning of such terms unless specifically indicated.

The term "distinguishing region" refers to a region that is measurably different between loci. Such differences include, but are not limited to, single nucleotide polymorphisms (SNPs), differences in methylation status, mutations including point mutations and indels, short tandem repeats, copy number variants, and the like.

The term "genomic region" as used herein refers to any region of one or more loci that are normally found in a contiguous fashion in a genome. A genomic region may vary in size up to and including an entire chromosome.

The term "informative locus" as used herein refers to a locus with one or more distinguishing regions which is homozygous in one source and heterozygous in the other source within a mixed sample.

The terms "locus" and "loci" as used herein refer to a nucleic acid region of known location in a genome.

The term "maternal sample" as used herein refers to any sample taken from a pregnant mammal which comprises a maternal first source and a fetal second source of cell free nucleic acids (e.g., RNA or DNA).

The term "mixed sample" as used herein refers to any sample comprising cell free nucleic acids (e.g., DNA) from two or more sources in a single individual which can be distinguished based on informative loci. Exemplary mixed samples include a maternal sample (e.g., maternal blood, serum or plasma comprising both maternal and fetal DNA), and a peripherally-derived somatic sample (e.g., blood, serum or plasma comprising different cell types, e.g., hematopoietic cells, mesenchymal cells, and circulating cells from other organ systems). Mixed samples include samples with genomic material from two different sources, which may be sources from a single individual, e.g., normal and atypical somatic cells; cells that are from two different individuals, e.g., a sample with both maternal and fetal genomic material or a sample from a transplant patient that comprises cells from both the donor and recipient; or samples with nucleic acids from two or more sources from different organisms, e.g., the mammalian host and an infectious organism such as a virus, bacteria, fungus, parasite, etc.

As used herein "nucleotide" refers to a base-sugar-phosphate combination which is a monomeric unit of a nucleic acid sequence (DNA and RNA). A nucleotide sequence refers to identification of the particular base for the nucleotide.

The terms "sequencing", "sequence determination" and the like as used herein refers generally to any and all biochemical processes that may be used to determine the order of nucleotide bases in a nucleic acid.

The term "set of loci" when used to determine CNV for a genomic region refers to two or more loci that are located within or associated with a genomic region. The copy number variation within a particular genomic region can be determined by measuring the copy number of the loci within the set of loci, and their relationship allows identification of copy number variation for a genomic region.

The Invention in General

This invention relates to processes for calculating the CNV of one or more genomic regions by comparison of frequency of the genomic regions to the source contribution of nucleic acids from different sources within a mixed sample. The present invention uses systems that process empirical information provided for distinguishing regions of informative loci to determine contribution of cell free nucleic acids from different sources within a sample. The CNV can be determined for larger genomic regions using selected sets of loci which are located in or are associated with the genomic region of interest.

The CNV for a genomic region can be calculated by comparison of the copy number or frequency of the genomic region from a particular source to a calculated "baseline" level of the contribution of nucleic acids from that source in a mixed sample. Such baseline numbers are preferably empirically determined, as described in more detail herein, although a reference baseline level can be used in specific embodiments.

The processes of the invention in many embodiments utilize binomial probability distributions to determine the percentage of nucleic acids from the different sources in a mixed sample. Such binomial distributions can allow the calculation of source contribution of cell free nucleic acids from a first source and a second source in a mixed sample. This information can be used along with counts of genomic regions of interest to determine any change in copy number of the genomic regions that deviate from the relative source contribution of the nucleic acids from the minor and/or first source. For larger genomic regions, counts of two or more selected loci can be used to determine the copy number variation for the genomic region and, in certain aspects, to define the size of the region that displays CNV in the mixed sample.

The source contribution can be determined in the processes and systems of the invention through utilization of informative loci with distinguishing regions that allow differentiation of nucleic acids from the different sources. Detection of the frequency of these informative loci within a sample can be detected using multiple mechanisms, including hybridization. Preferably, source contribution of nucleic acids from different sources within a mixed sample is determined by sequence determination of the isolated copies of nucleic acids corresponding to informative loci from the sources in the mixed sample. The number of individual informative loci used to determine source contribution may be 2 or more, preferably 4 or more, preferably 8 or more, preferably 16 or more, preferably 32 or more, preferably 64 or more, and most preferably 96 or more.

Multiple mechanisms for identifying the distinguishing regions within an informative locus can be used in the processes of the invention. For example, source contribution of cell free DNA in a sample from a single individual can be determined by sequencing copies of two or more informative loci present in a mixed sample. For each informative locus, counts for both alleles (signified herein as A and B) present in the mixed sample are determined. With an observation of counts $A \leq B$, A is the count for the less abundant allele of the informative locus (corresponding to the second source DNA) and B is the count for the more abundant allele (corresponding to the first source DNA).

Statistically, this environment is modeled by a binomial distribution with some probability p of sequencing the A allele in a mixture of A and B alleles:

$$\text{Binomial}(A, B, p) = \frac{(A+B)!}{A!B!} p^A (1-p)^B.$$

Since A and B are known, the probability p is the informative value. The value p* of p that maximizes the value of Binomial(A, B, p) is considered the maximum likelihood estimate for the binomial distribution with counts A and B.

For example, since fetal DNA is expected to be less prevalent in maternal plasma, the probability p of sequencing the A allele corresponds to a measure of fetal enrichment f using the following formula:

$f=2*p.$

The best (most likely) estimate of fetal enrichment given the A and B counts is when p=p*.

A more accurate calculation of the source contribution of cell free nucleic acids from a mixed sample can be calculated using sequence determination of several informative loci within the mixed sample. The use of multiple loci in determining second source percent DNA contribution increases the likelihood that the percentage is truly representative, as measurement of frequency of a single informative locus may not be truly indicative of the level of all second source DNA.

In order to determine the percentage of cell free nucleic acids from a first source and/or a second source within a mixed sample, the sequence of a statistically significant number of copies of several informative loci is determined. The counts of the different polymorphisms in the loci are used to calculate the source contribution of the cell free nucleic acids from the sources within the mixed sample, with $A_i$ and $B_i$ representative of the counts of the A and B alleles for the ith locus. For example, for 20 informative loci sequenced, each one individually is referred to as the 1st, 2nd, 3rd, ..., 20th. Thus $A_5$ and $B_5$ are the counts for the A and B alleles of the 5th locus.

The probability p of sequencing A alleles from these multiple measurements corresponds to a measure of enrichment of the DNA from the second source. Each $A_i$, $B_i$ pair of counts for the ith locus, however, has a different best estimate $p_i^*$ for the probability of sequencing an A allele. This is addressed by utilizing the product of many binomial distributions corresponding to informative loci that have been measured:

$$\prod_i \text{Binomial}(A_i, B_i, p).$$

The value of p that maximizes this product is denoted $p^*$, and just as before gives the best estimate of enrichment of the second source DNA when $p=p^*$. The $p^*$ can be identified using any number of standard optimization algorithms, as described in more detail below. Frequently a logarithmic transformation is applied to the product to make the computations easier, while still producing the same result.

In a more specific example, an accurate estimation of fetal DNA frequency can be determined using the processes of the invention with a relatively tight confidence interval, regardless of the gender of the fetus. This approach differs from processes which utilize Y chromosome sequences derived from male fetuses for fetal frequency estimation (Fan et al., Proc Natl Acad Sci USA. 2008 Oct. 21; 105(42):16266-71. Epub 2008 Oct. 6; Lun F M et al., Proc Natl Acad Sci USA. 2008 Dec. 16; 105(50):19920-5. Epub 2008 Dec. 5). This approach also differs from other processes in that it employs a direct allelic identification approach rather than an indirect measure of either probe hybridization during real time PCR (Lun F M et al., Clin Chem. 2008 October; 54(10):1664-72. Epub 2008 Aug. 14) or band intensity following electrophoresis (Dhallan et al., Lancet. 2007 Feb. 10; 369(9560):474-81). Importantly, the invention utilizes multiple informative loci to determine fetal allele frequency, and the accuracy of the estimation can be improved by reducing the deviation of the different best estimate $p_i^*$ for each individual locus. Accuracy can also be increased by using additional loci in determination of p.

Detection of informative loci for use in the processes of the invention can be carried out using various techniques known to those skilled in the art. These include, but are not limited to, those described in U.S. Pat. No. 6,258,540, issued to Lo and Wainscoat; U.S. Pat. Nos. 7,901,884, 7,754,428, 7,718,367, 7,709,194, and 7,645,576 issued to Lo et al; U.S. Pat. No. 7,888,017 issued to Quake et al.; Chiu R W, et al. 2008. U.S. Pat. Nos. 7,727,720 and 7,718,370, 7,442,506, 7,332,277, 7,208,274 and 6,977,162, issued to Dhallan; U.S. Pat. No. 7,799,531, issued to Mitchell and Mitchell; U.S. Pat. No. 7,582,420, issued to Oliphant et al. U.S. application Ser. No. 13/013,732 (Oliphant et al.), Proc Natl Acad Sci USA 105: 20458-20463; Dhallan et al. 2007 Lancet 369: 474-481; Fan H C et al., 2008 Proc Natl Acad Sci 105:16266-16271; Fan H C et al., 2010 Clinical Chemistry 56:8; 1279-1286 Lo Y M et al., Proc Natl Acad Sci USA 104: 13116-13121; Lun F M, Chiu R W et al., 2008 Clin Chem 54: 1664-1672; Lun F M et al., Proc Natl Acad Sci USA 105: 19920-19925, each of which are incorporated by reference herein.

In a preferred aspect, the distinguishing regions of the informative loci in the mixed sample are detected in a manner to maximize the counts detected for A and B values of each informative locus. This can be done, for example, by performing multiple identification reactions for the distinguishing regions at each locus. This reduces the bias in allele count that may be introduced from the experimental activities used to obtain the counts. The estimation of second source DNA is thus more accurate with a tighter confidence interval.

FIG. 1 is a block diagram illustrating an exemplary system environment in which one embodiment of the present invention may be implemented for determining contribution of cell free nucleic acids from the first source and/or second source in a mixed sample. The system 10 includes a DNA sequencer 12, a server 14 and a computer 16. The DNA sequencer 12 may be coupled to the server 14 and/or the computer directly or through a network. The computer 16 may be in communication with the server 14 through the same or different network.

In one embodiment, a mixed sample 18 is input to the DNA sequencer 12. In one embodiment, the mixed sample 18 may comprise maternal and fetal cell free nucleic acids that contain cell free nucleic acids from normal cells and cancer cells. The DNA sequencer 12 may be any commercially available instrument that automates the DNA sequencing process for sequence analysis of oligonucleotides present in the mixed sample 18. The output of the DNA sequencer 12 may be in the form of first and second data sets 20 comprising frequency data for one or more informed and loci from first and second sources. In one embodiment, the first and second data sets 20 may be stored in a database 22 that is accessible by the server 14.

According to the exemplary embodiment, the computer 16 executes a software component, referred to herein as the copy number variation (CNV) application 24, that calculates CNV for one or more genomic regions in the mixed sample 18 by comparison of frequency of the genomic regions to the source contribution of nucleic acids from different sources within the mixed sample 18. In one embodiment, the computer 16 may comprise a personal computer, but the computer 16 may comprise any type of machine that includes at least one processor and memory.

The output of the copy number variation application 24 is a report 26 listing the CNV. The report 26 may be paper that is printed out, or electronic, which may be displayed on a monitor and/or communicated electronically to users via e-mail, FTP, text messaging, posted on a server, and the like.

Although the application 24 is shown as being implemented as software, the application 24 may be implemented as a combination of hardware and software. In addition, the application 24 may be implemented as multiple components operating on the same or different computers.

Both the server 14 and the computer 16 may include hardware components of typical computing devices (not shown), including a processor, input devices (e.g., keyboard, pointing device, microphone for voice commands, buttons, touchscreen, etc.), and output devices (e.g., a display device, speakers, and the like). The server 14 and computer 16 may include computer-readable media, e.g., memory and storage devices (e.g., flash memory, hard drive, optical disk drive, magnetic disk drive, and the like) containing computer instructions that implement the functionality disclosed when executed by the processor. The server 14 and the computer 16 may further include wired or wireless network communication interfaces for communication.

Although the server 14 and computer 16 are shown as single computers, it should be understood that they could be multiple servers and computers, and the functionality of the copy number variation application 24 may be implemented using a different number of software components. For example, the copy number variation application 24 may be implemented as more than one component.

Optimization Algorithms for Use with the Invention

The probability p* that provides the best fit for p in the determination of the maximum likelihood estimate can be further refined using an optimization algorithm. Thus, in a preferred embodiment, the maximum likelihood estimate is calculated using an optimization algorithm to provide an iterative process for determining probability p that best fits the data of the two data sets. The optimization algorithm can be any algorithm that can determine the best fit for probability p based on the empirical informative loci data. Examples of such optimization algorithms include gradient descent, simulated annealing, or evolutionary algorithms. Simulated annealing (SA) is a generic probabilistic metaheuristic for the global optimization problem of locating a good approximation to the global optimum of a given function in a large search space. It is often used when the search space is discrete (e.g., all tours that visit a given set of cities). For certain problems, simulated annealing may be more effective than exhaustive enumeration—provided that the goal is merely to find an acceptably good solution in a fixed amount of time, rather than the best possible solution.

In other aspects, the algorithm is an evolutionary algorithm, which is a search heuristic that mimics the process of natural evolution. Evolutionary algorithms generate solutions to optimization problems using techniques inspired by natural evolution, such as inheritance, mutation, selection, and crossover.

In yet other aspects, the algorithm used in gradient descent, also known as steepest descent, or the process of steepest descent. Gradient descent is a first-order optimization algorithm. To find a local minimum of a function using gradient descent, one takes steps proportional to the negative of the gradient (or of the approximate gradient) of the function at the current point. If instead one takes steps proportional to the positive of the gradient, one approaches a local maximum of that function.

EXAMPLES

The following examples are put forth so as to provide those of ordinary skill in the art with a complete disclosure and description of how to make and use the present invention, and are not intended to limit the scope of what the inventors regard as their invention, nor are they intended to represent or imply that the experiments below are all of or the only experiments performed. It will be appreciated by persons skilled in the art that numerous variations and/or modifications may be made to the invention as shown in the specific aspects without departing from the spirit or scope of the invention as broadly described. The present aspects are, therefore, to be considered in all respects as illustrative and not restrictive.

Efforts have been made to ensure accuracy with respect to numbers used (e.g., amounts, temperature, etc.) but some experimental errors and deviations should be accounted for.

Example 1

Calculation of Source Contribution Using a Single Locus

In order to determine the percentage of a cfDNA from a single source within a mixed sample, the sequence of a statistically significant number of copies of an informative locus is determined. The counts of the different polymorphisms in the loci are used to calculate the source contribution of the cfDNA from the first source and/or the second source within the mixed sample.

In an informative locus with a single polymorphism, following sequence determination of the first allele (A) and the second allele (B), the number of alleles present in the sample are found empirically to be A=10 and B=100. The source contribution (p) of the second source allele, A, is determined using the following equation:

$$\text{Binomial}(10, 100, p) = \frac{110!}{10!100!} p^{10}(1-p)^{100}.$$

For optimization, the mle function of the R statistical software system, version release 2.12.2 was used to perform all binomial calculations. Using the mle function in the R statistical software system, p* was estimated to be 0.09091285, which corresponds to a fetal enrichment of f=2*p*=0.1818257.

Example 2

Calculation of Second Source Contribution Using Multiple Loci

In order to determine the percentage of cfDNA from a single source within a mixed sample using multiple loci, the sequence of a statistically significant number of copies of two or more informative loci were determined. The counts of the different polymorphisms in the loci were used to calculate the source contribution of the cfDNA from the first source and/or the second source within the mixed sample.

In a first example using multiple loci from a maternal sample comprising both maternal and fetal cfDNA, five informative loci with the following counts for the A and B alleles were determined empirically:

| I | $A_i$ | $B_i$ |
|---|---|---|
| 1 | 10 | 100 |
| 2 | 8 | 90 |
| 3 | 11 | 99 |
| 4 | 13 | 124 |
| 5 | 9 | 113 |

As reported the maximum likelihood estimate is:

$p^*=0.08839108$ and the fetal % is $f=2*p^*=0.1767822$

The process of the invention was then used to find the p* that maximizes the product:
Binomial(10,100,p)*Binomial(8,90,p)*Binomial(11,99,p)*
Binomial(13,124,p)*Binomial(9,113,p).

Using the mle function in the R statistical software system, version release 2.12.2, the p* was estimated to be 0.08839108, corresponding to a fetal enrichment estimate of $$f = 2 * p^* = 0.1767822$$

Example 3

Calculation of CNV of an Informative Locus

The approach described in Example 2 using binomials was used to determine source contribution of fetal nucleic acids in a maternal sample. In addition, a more standard ratio-based method described in Chu et al., *Prenat Diagn* 2010; 30: 1226-1229 was also used to derive an estimation of the percent fetal contribution in a maternal sample. These numbers generated empirically from which the percent fetal contribution was determined were in turn used to identify loci in which the CNV varied by at least 50% from the estimated source contribution of the fetal DNA in the maternal sample. Table 1 summarizes the data and the calculation of percent fetal in the sample:

TABLE 1

Determination of Percent Fetal cfDNA for a First Maternal Sample Using 49 Informative Loci

| Sample 1 | Loci | $A_i$ Counts | $B_i$ Counts | Binomial Percent Fetal Calculation | Chu et al., Percent Fetal Calculation |
|---|---|---|---|---|---|
| | Ch01_Lc1 | 42 | 793 | 0.078836119 | 0.078820769 |
| | Ch01_Lc2 | 34 | 744 | | |
| | Ch01_Lc3 | 22 | 927 | | |
| | Ch01_Lc4 | 28 | 552 | | |
| | Ch01_Lc5 | 13 | 826 | | |
| | Ch01_Lc6 | 37 | 753 | | |
| | Ch01_Lc7 | 44 | 784 | | |
| | Ch01_Lc8 | 18 | 482 | | |
| | Ch02_Lc1 | 36 | 998 | | |
| | Ch02_Lc2 | 52 | 1206 | | |
| | Ch02_Lc3 | 45 | 844 | | |
| | Ch03_Lc1 | 40 | 869 | | |
| | Ch03_Lc2 | 20 | 516 | | |
| | Ch03_Lc3 | 35 | 851 | | |
| | Ch03_Lc4 | 21 | 785 | | |
| | Ch03_Lc5 | 64 | 1020 | | |
| | Ch03_Lc6 | 33 | 979 | | |
| | Ch03_Lc7 | 30 | 1159 | | |
| | Ch04_Lc1 | 28 | 499 | | |
| | Ch04_Lc2 | 47 | 810 | | |
| | Ch04_Lc3 | 18 | 587 | | |
| | Ch05_Lc1 | 61 | 1191 | | |
| | Ch05_Lc2 | 15 | 899 | | |
| | Ch05_Lc3 | 21 | 566 | | |
| | Ch05_Lc4 | 40 | 772 | | |
| | Ch05_Lc5 | 36 | 1031 | | |
| | Ch06_Lc1 | 41 | 822 | | |
| | Ch06_Lc2 | 65 | 1078 | | |
| | Ch07_Lc1 | 31 | 831 | | |
| | Ch07_Lc2 | 39 | 857 | | |
| | Ch07_Lc3 | 48 | 1148 | | |
| | Ch07_Lc4 | 25 | 876 | | |
| | Ch08_Lc1 | 39 | 869 | | |
| | Ch08_Lc2 | 17 | 491 | | |
| | Ch08_Lc3 | 31 | 585 | | |
| | Ch08_Lc4 | 42 | 840 | | |
| | Ch08_Lc5 | 47 | 963 | | |
| | Ch09_Lc1 | 20 | 571 | | |
| | Ch09_Lc2 | 25 | 692 | | |
| | Ch09_Lc3 | 23 | 543 | | |
| | Ch09_Lc4 | 32 | 742 | | |
| | Ch09_Lc5 | 20 | 988 | | |
| | Ch10_Lc1 | 28 | 555 | | |
| | Ch10_Lc2 | 15 | 664 | | |
| | Ch10_Lc3 | 11 | 814 | | |
| | Ch11_Lc1 | 39 | 1036 | | |
| | Ch11_Lc2 | 38 | 661 | | |
| | Ch11_Lc3 | 34 | 779 | | |
| | Ch12_Lc1 | 38 | 713 | | |
| | Ch12_Lc2 | 35 | 973 | | |

To identify loci exhibiting a statistically significant decrease in copy numbers of loci detected, the ratio of the individual loci was determined and compared to the calculated percent fetal cfDNA for the maternal sample. The numbers shown bolded above each displayed significantly lowered copy number of fetal DNA compared to the frequency of the maternal allele. The overall percent calculation of fetal cfDNA in the maternal sample was 7.8%. The following loci exhibited a fetal contribution 5-fold or less than the average, and thus a statistically decreased CNV:

| Locus | Fetal Cts | Maternal Cts | Ave % fetal | Locus % fetal | % Decrease |
|---|---|---|---|---|---|
| Ch01_Lc5 | 13 | 826 | 7.88% | 1.57% | 5.02-fold |
| Ch10_Lc3 | 11 | 814 | 7.88% | 1.35% | 5.84-fold |

The algorithm used for optimization of the maximum likelihood estimate was the "Broyden, Fletcher, Goldfarb, and Shanno" ("BFGS") method. The BFGS method is a gradient descent algorithm that approximates Newton's method. For optimization, the mle function of the R statistical software system, version release 2.12.2 was used to perform all binomial calculations.

When compared to a weighted average approach introduced by Chu et al., the maximum likelihood estimate results from the binomial distribution approach presented above correlated with an $R2>0.99$ and a slope near 1.

Example 3

Calculation of CNV of a Genomic Region

As described above, the approach described in Example 2 using binomials was used to determine source contribution of fetal nucleic acids in a maternal sample.

In a separate assay, the mixed sample was analyzed for loci found within the DiGeorge Syndrome Critical Region (DGCR) at chromosome 22q11. These loci include two loci on either end of the velo-cardio facial syndrome region at 22q11.2, and the loci known to be involved in conotruncal cardiac disease. A total of 32 loci in all spanning the DGCR are used to determine the presence of a possible deletion and the boundaries of any deletion that may be present in a mixed sample.

In a first sample, the percent fetal DNA in the maternal sample is determined to be approximately 9.2% using the methods of Example 2. The loci in the DGCR are differentiated in the maternal and fetal sources in a separate assay through the identification of polymorphisms in the selected loci of the set used to determine the presence or absence of a deletion at 22q11. All fetal 22q11 loci of the set of selected loci spanning the DGCR are found to be present in the maternal sample at a variance of from approximately 8.9-9.3% of the total amount of selected loci in the maternal sample, and so no deletion is detected in this sample.

In a second sample, the percent fetal DNA in the maternal sample is determined to be approximately 10.4% using the methods of Example 2. All fetal 22q11 loci of the set of selected loci are found to be present in the maternal sample at a variance of from approximately 4.8-5.4% of the total amount of selected loci in the maternal sample. This is consistent with a deletion of one DGCR at chromosome 22 from paternal origin.

A process and system for estimating copy number variation of selected loci from a first source and a second source in a mixed sample has been disclosed. The present invention has been described in accordance with the implementations shown, and there could be variations to the implementations, and any variations would be within the spirit and scope of the present invention. For example, the exemplary embodiment can be implemented using hardware, software, a computer readable medium containing program instructions, or a combination thereof. Software written according to the present invention is to be either stored in some form of computer-readable medium such as a memory, a hard disk, or a CD/DVD-ROM and is to be executed by a processor. Accordingly, many modifications may be made by one of ordinary skill in the art without departing from the spirit and scope of the appended claims. In the claims that follow, unless the term "means" is used, none of the features or elements recited therein should be construed as means-plus-function limitations pursuant to 35 U.S.C. §112, ¶16.

What is claimed is:

1. A computer-implemented process for determining copy number variation (CNV) of a one or more genomic regions in a single source in a mixed sample, wherein at least one processor coupled to a memory executes a software component that performs the process comprising:
    accessing by the software component a first data set comprising frequency data based on identification of distinguishing regions of two or more informative loci from a first source in the single source in the mixed sample;
    accessing by the software component a second data set comprising frequency data based on identification of distinguishing regions of two or more informative loci from a second source in the single source in the mixed sample;
    calculating by the software component an estimated source contribution of cell free nucleic acids based on a binomial distribution of counts of the distinguishing regions from first and second data sets;
    accessing by the software component a third data set comprising frequency data for one or more genomic regions from the single source in the mixed sample; and
    calculating by the software component a presence or absence of a CNV for the one or more genomic regions by comparison of the frequency data from the single source to the estimated contribution of cell free nucleic acids in the mixed sample.

2. The process of claim 1, wherein the CNV is calculated based on empirical frequency data for the one or more genomic regions from the single source in the mixed sample.

3. A computer-implemented process for determining copy number variation (CNV) of one or more genomic regions a single source in a mixed sample, wherein at least one processor coupled to a memory executes a software component that performs the process, the process comprising:
    accessing by the software component a first data set comprising frequency data for one or more informative loci from a maternal source in the mixed sample;
    accessing by the software component a second data set comprising frequency data for one or more informative loci from a fetal source in the mixed sample;
    calculating by the software component an estimated fetal source contribution of cell free nucleic based on a binomial distribution of the counts of distinguishing regions from first and second data sets; and
    accessing by the software component a third data set comprising frequency data for one or more genomic regions from the single source in the mixed sample; and
    calculating by the software component the presence or absence of a CNV for the one or more genomic regions in the fetus by comparison of the frequency of the genomic regions from the single source to the estimated fetal source contribution of cell free nucleic acids in the mixed sample.

4. An executable software product stored on a non-transitory computer-readable medium containing program instructions, which when executed by a computer directs performance of steps for estimating copy number variation (CNV) of one or more genomic regions in a mixed sample, the steps comprising:
    accessing by the software component a first data set comprising frequency data based on identification of distinguishing regions from copies of one or more informative loci from a first source;
    accessing by the software component a second data set comprising frequency data based on identification of distinguishing regions from copies of one or more informative loci from a second source;
    calculating by the software component an estimated source contribution of cell free nucleic acids based on a binomial distribution of the first and second data sets; and
    calculating by the software component the CNV for the one or more genomic regions by comparison of the at least one of the first source and the second source counts for the genomic region to the estimated source contribution of cell free nucleic acids from the at least one of the first source and the second source.

5. The process of claim 4, wherein the CNV is calculated based on empirical frequency data for the one or more genomic regions from the single source in the mixed sample.

6. A system, comprising:
    a memory;
    a processor coupled to the memory; and
    a software component executed by the processor that is configured to:
    access a first data set comprising frequency data based on identification of distinguishing regions from copies of one or more informative loci from a first source in a mixed sample;
    access a second data set comprising frequency data based on identification of distinguishing regions from copies of one or more informative loci from a second source in the mixed sample;

calculate an estimated contribution of cell free nucleic acids from at least one of the first source and the second source based on a binomial distribution of counts of the distinguishing regions from the first and second data sets; and calculate a copy number variation for one or more genomic regions of a single source in the mixed sample by comparison of the frequency data for the one or more genomic regions to the estimated source contribution of cell free nucleic acids in the mixed sample.

7. A computer software product including a non-transitory computer-readable storage medium having fixed therein a sequence of instructions which when executed by a computer directs performance of steps of:

creating a first data set representing a quantity of informative loci from a first source in a mixed sample;

creating a second data set representing a quantity of informative loci from a second source in a the mixed sample;

calculating an estimated source contribution of cell free nucleic acids from the first source and the second source in the mixed sample based on a binomial distribution of the quantities of informative loci from the first and second data sets; and calculating a presence or absence of a copy number variation for a genomic region by comparison of the quantity of one or more informative loci from the first and second data sets to the estimated source contribution of cell free nucleic acids in the mixed sample.

* * * * *